United States Patent
Hutter et al.

(10) Patent No.: US 9,878,322 B2
(45) Date of Patent: Jan. 30, 2018

(54) PIPETTING UNIT AND METHOD OF PIPETTING A TEST LIQUID

(71) Applicant: Roche Diagnostics Operations, Inc., Indianapolis, IN (US)

(72) Inventors: Roland Hutter, Zug (CH); Roland Stoeckli, Boswil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 307 days.

(21) Appl. No.: 14/047,230

(22) Filed: Oct. 7, 2013

(65) Prior Publication Data

US 2014/0106467 A1   Apr. 17, 2014

(30) Foreign Application Priority Data

Oct. 12, 2012   (EP) .................................... 12188267

(51) Int. Cl.
  *B01L 3/00*   (2006.01)
  *B01L 3/02*   (2006.01)
  *G01N 35/10*   (2006.01)

(52) U.S. Cl.
  CPC .......... *B01L 3/021* (2013.01); *G01N 35/1004* (2013.01); *G01N 35/1016* (2013.01); *B01L 2200/0615* (2013.01); *B01L 2200/0684* (2013.01); *B01L 2200/141* (2013.01); *B01L 2200/146* (2013.01); *B01L 2400/0487* (2013.01); *G01N 2035/1018* (2013.01); *Y10T 436/2575* (2015.01)

(58) Field of Classification Search
  CPC ............................ G01N 35/1004; B01L 3/021

USPC ........................................................ 436/180
See application file for complete search history.

(56) References Cited

U.S. PATENT DOCUMENTS

| | | | |
|---|---|---|---|
| 6,370,942 B1* | 4/2002 | Dunfee .............. | G01N 35/1016 73/1.74 |
| 2010/0000343 A1* | 1/2010 | Gagnaux ................ | G01N 35/10 73/864.21 |
| 2010/0047128 A1* | 2/2010 | Mototsu .................... | B08B 3/02 422/63 |
| 2010/0051060 A1* | 3/2010 | Kuroda .............. | G01N 35/1004 134/22.11 |

FOREIGN PATENT DOCUMENTS

| | | |
|---|---|---|
| EP | 0747689 B1 | 12/1996 |
| EP | 2157435 A1 | 2/2010 |
| JP | 54-155088 A | 12/1979 |

(Continued)

*Primary Examiner* — Christine T Mui
*Assistant Examiner* — Emily R. Berkeley
(74) *Attorney, Agent, or Firm* — Roche Diagnostics Operations, Inc.

(57) ABSTRACT

A pipetting unit and a method of using the pipetting unit for pipetting a volume V1 of test liquid for carrying out an in vitro diagnostic test are presented. The method comprises dipping a nozzle of a pipetting unit into a test liquid and aspirating a volume V4 of the test liquid larger than the volume V1 required for carrying out the test. The method further comprises dipping the pipetting unit into a wash liquid and dispensing a volume V2 equal or smaller than V4 minus V1 of the test liquid into the wash liquid. The method further comprises dipping the pipetting unit into a reaction liquid and dispensing the volume V1 of test liquid required for the test.

5 Claims, 1 Drawing Sheet

(56) References Cited

FOREIGN PATENT DOCUMENTS

| JP | S54-155088 | A | 12/1979 |
| JP | 57-208461 | A | 12/1982 |
| JP | S57-208461 | A | 12/1982 |
| JP | S62-228954 | A | 10/1987 |
| JP | 2007-212399 | A | 8/2007 |
| WO | 01/88549 | A1 | 11/2001 |

* cited by examiner

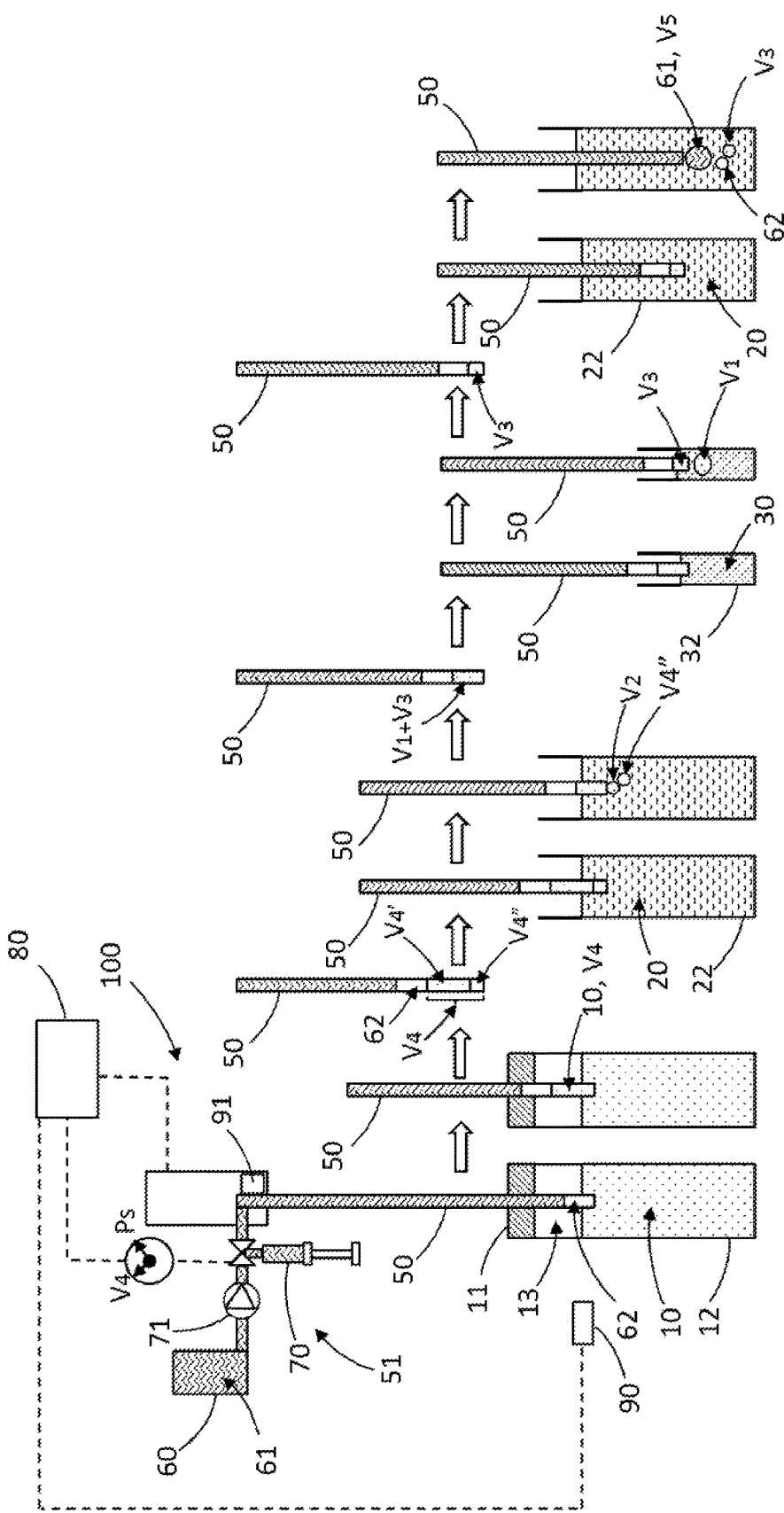

PIPETTING UNIT AND METHOD OF PIPETTING A TEST LIQUID

CROSS-REFERENCE TO RELATED APPLICATIONS

This application is a continuation of EP 12188267.4, filed Oct. 12, 2012, which is hereby incorporated by reference.

BACKGROUND

The present disclosure generally relates to a pipetting unit and method for pipetting a volume of test liquid and, in particular, to a pipetting unit and method for pipetting a volume of test liquid for carrying out an in vitro diagnostic test such as, for example, a coagulation test.

Different types of pipetting units and pipetting methods have been implemented in various analytical instruments. Among the various pipetting methods, the most challenging ones are those requiring aspirating a volume of test liquid through a cap of a test liquid container. This is typically done by piercing with the nozzle of the pipetting unit a septum of elastomeric material sealing a test liquid container, in which the test liquid is contained. Precision of volume and reproducibility may be particularly hard to achieve when the test liquid container is partially evacuated and/or the volume to be aspirated is small, e.g. below 5-10 microliters. This is due to the fact that air may be present in the pipetting unit and also to the fact that negative pressure, i.e. a pressure lower than atmospheric pressure, is present in the liquid container. This negative pressure, which may be different from container to container, may have an effect on the air in the pipetting unit. This in turn may affect the actual volume of liquid being aspirated and the position of the aspirated volume in the pipetting unit. This means that a first pipetting error may occur when aspirating (a wrong volume) and a second pipetting error may occur when dispensing (wrong position) possibly resulting in only part of the aspirated test liquid being dispensed or no test liquid at all being dispensed.

In order to improve precision of pipetting, the pipetting unit may be operated with a system liquid, in which the presence of air in the pipetting unit is minimized. However a small amount of air, may be still dispersed in the system liquid, e.g. in the form of microbubbles. Air is typically present also at the extremity of the nozzle e.g. due to evaporation of system liquid or on purpose by aspirating a plug of air in order to separate the system liquid from the test liquid to be aspirated. This air, which is affected by the pressure conditions inside the container, may be the major responsible for pipetting errors especially for small volumes as mentioned above.

An additional potential source of errors is the wetting of the outside of the nozzle, i.e. the tip and sides of the nozzle, when aspirating the test liquid. Also, when withdrawing the nozzle through the cap of the container, liquid may be present on the underneath of the cap resulting in loss of aspirating liquid or in additional pick up of liquid, either via the inside or outside of the nozzle.

One way to partly solve this problem is to aspirate an excess of test liquid and discard a first volume, possibly comprising air and test liquid, before dispensing the volume required for the test into a reaction vessel.

Dispensing is normally done by positioning the pipetting nozzle above a waste compartment and above the reaction vessel respectively. The pipetting nozzle is then washed from outside by dipping the nozzle into a wash liquid and from inside by flushing system liquid before aspirating another test liquid. This way of dispensing is also prone to errors because of surface effects at the tip and sides of the nozzle.

Therefore, there is a need for a pipetting unit and method which provide a more reproducible and more precise pipetting of test liquids regardless of the volume required for the test and the type of test liquid container.

SUMMARY

According to the present disclosure, a pipetting unit and method for pipetting a volume (V1) of test liquid for carrying out an in vitro diagnostic test is presented. The method comprises dipping a nozzle of a pipetting unit into a test liquid and aspirating a volume (V4) of the test liquid larger than the volume V1 required for carrying out the in vitro diagnostic test, dipping the nozzle into a wash liquid and dispensing a volume (V2) equal or smaller than V4 minus V1 of the test liquid into the wash liquid, and dipping the nozzle into a reaction liquid and dispensing the volume V1 of test liquid required for the in vitro diagnostic test.

Accordingly, it is a feature of the embodiments of the present disclosure to provide a pipetting unit and method that provide a more reproducible and more precise pipetting of test liquids regardless of the volume required for the test and the type of test liquid container. Other features of the embodiments of the present disclosure will be apparent in light of the description of the disclosure embodied herein.

BRIEF DESCRIPTION OF THE DRAWING

The following detailed description of specific embodiments of the present disclosure can be best understood when read in conjunction with the following drawing, where like structure is indicated with like reference numerals and in which:

FIG. 1 illustrates schematically, and not to scale, an example of pipetting unit and method of pipetting a volume of test liquid for carrying out an in vitro diagnostic test (steps indicated by arrows from left to right) according to an embodiment of the present disclosure.

DETAILED DESCRIPTION

In the following detailed description of the embodiments, reference is made to the accompanying drawing that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure refers to a method of pipetting a volume V1 of test liquid for carrying out an in vitro diagnostic test. The method can comprise dipping a nozzle of a pipetting unit into a test liquid and aspirating a volume V4 of the test liquid larger than the volume V1 required for carrying out the test. The method can further comprise dipping the nozzle into a wash liquid and dispensing a volume V2 equal or smaller than V4 minus V1 (V4−V1) of the test liquid into the wash liquid. The method can further comprise dipping the nozzle into a reaction liquid and dispensing the volume V1 of test liquid, which can be required for the test.

The term "test liquid" can be herein used to indicate either a sample or a reagent or both, such as, for example, a mixture or solution of one or more samples and one or more reagents. The term "sample," as used herein, can refer to a liquid material suitable for being pipetted and being subjected to an in vitro diagnostic test, e.g. in order to detect one or more analytes of interest suspected to be present therein or to measure a physical parameter of the sample such as, for example, pH, color, turbidity, viscosity, coagulation time, or the like. Examples of in vitro diagnostic tests are clinical chemistry assays, immunoassays, coagulation assays, nucleic acid testing, and the like. This method can particularly be suitable for coagulation in vitro diagnostic tests. Typically, in vitro coagulation tests can be the determination of Thrombocyte/Platelet count (Plt), of the mean platelet volume (MPV), of the prothrombin time (PT), of the activated partial thromboplastin time (APTT), of the thrombin clotting time (TCT), of Fibrinogen, of Antithrombin III (AT III), of the viscosity, or any other suitable test. For these kinds of tests, the concentration of analytes present in the test liquid can typically be large enough, e.g. compared to immunochemical tests, that traces of such analytes from another test liquid due to carryover play a negligible role in the final result of the test. On the other hand, due to the high concentration of analytes, it can be important that the volume $V1$ of test liquid used for the test be as precise as possible.

The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells, or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more in vitro diagnostic tests. The term "sample" as used herein can therefore be not only used for the original sample but can also relate to a sample which has already been processed (pipetted, diluted, mixed with reagents, enriched, having been purified, having been amplified and the like). In the case of coagulation tests, the sample can typically be plasma from blood treated with citrate.

The term "reagent" can be used to indicate a composition required for treatment of a sample. Reagents may be any liquid, e.g. a solvent or chemical solution, which may need to be mixed with a sample and/or other reagent in order e.g. for a reaction to occur, or to enable detection. A reagent may be for example a diluting liquid, including water, it may comprise an organic solvent, it may comprise a detergent, it may be a buffer. A reagent, in the more strict sense of the term, may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, and the like.

A "reaction liquid," can herein be used to indicate a liquid to be reacted with the test liquid in order to carry out an in vitro diagnostic test. Thus, a "reaction liquid" may be any of the three following options, depending on the nature of the test liquid. According to a first option, the test liquid can be a sample and the reaction liquid can be a liquid containing at least one reagent. According to a second option, the test liquid can be a reagent and the reaction liquid can comprise at least one sample and optionally at least one reagent. According to a third option, the test liquid can be a liquid comprising at least one sample and at least one reagent and the reaction liquid can be a liquid comprising at least one reagent.

The term "pipetting" can herein be used to indicate aspirating, i.e. withdrawing, a volume of test liquid in a first step and dispensing a volume of test liquid in a second step, wherein the volume of dispensed liquid may be different from the volume of aspirated liquid and wherein intermediate aspirating and/or dispensing steps may occur between the first step and the second step.

A "pipetting unit" can thus be a device comprising at least one aspiration/dispensing nozzle and assisting the user with the automatic pipetting of volumes of test liquids.

Samples can typically be provided in test liquid containers such as sample tubes and therefore typically aspirated from sample tubes. A "sample tube," can be either a sample collection test tube, also called "primary tube," which can be used to receive a sample from a patient and to transport the sample contained therein to an analytical laboratory for an in vitro diagnostic test, or a "secondary tube," which may be used to receive an aliquot of sample from a primary tube. Sample tubes such as the primary tubes may be closed by a cap and may be partially evacuated. The cap may comprise a pierceable elastomeric material.

Reagents can typically be provided in different types of test liquid containers such as reagent cassettes, bottles or packages, comprising one or more reagent compartments comprising one or more different types of reagents, e.g. kits of reagents required for particular in vitro diagnostic tests. Reagent containers can typically be closed by a cap, e.g. to prevent evaporation and minimize the risk of contamination from the environment. The cap may be opened and reclosed, e.g. every time that a volume of reagent needs to be aspirated. The cap may alternatively be pierced so that aspiration may occur through the cap. Aspirating a test liquid may thus comprise penetrating a cap of a test liquid container and aspirating a volume of test liquid through the cap. This volume can be referred to as $V4$.

In order to aspirate a volume of test liquid, the method can comprise dipping the nozzle of the pipetting unit into the test liquid. This can mean moving the nozzle towards and into the test liquid so that the nozzle may be positioned at a depth below the surface, which can be sufficient for aspirating the desired volume while minimizing contact of the outside of the nozzle with the test liquid. This depth can typically be in the order of a few millimeters, e.g. less than about 5 mm in order to minimize contact of the outside of the nozzle with the test liquid. In this way, the risk of carryover and/or pipetting errors due to external wetting of the nozzle can further be reduced. The volume $V4$ of aspirated test liquid can be larger than the volume $V1$ required for carrying out the test. The volume $V4$ can be a nominal volume, meaning that the pipetting unit can be operated such as to pump in, i.e. aspirate, a volume $V4$. However, the effectively aspirated volume $V4$ may larger or smaller than the nominal volume. It may e.g. comprise also air and therefore $V4$ may be the sum of a volume $V4'$ of test liquid and a volume of air $V4''$. $V4$ can however be sufficiently large so that a volume of test liquid larger than the volume $V1$ required for the test can be effectively aspirated.

The method can further comprise dipping the nozzle into a wash liquid after aspirating the volume $V4$ and dispensing a volume $V2$ equal or smaller than $V4$ minus $V1$ of the test liquid into the wash liquid.

A "wash liquid" can herein be used to indicate a liquid for washing the pipetting unit and, in particular, at least that part of the external surface of the pipetting unit, which has been dipped into the test liquid in the previous aspiration step, i.e. at least part of the nozzle. This can mean moving the nozzle towards and into the wash liquid so that the nozzle can be positioned at a depth below the surface, which can be sufficient for washing that part of the outside of the nozzle contacted by the test liquid. The wash liquid can at least partially fill a wash chamber or vessel or can flush through a wash chamber so that the part of the nozzle to be washed can be contacted by the wash liquid when the nozzle is dipped into the wash liquid. The wash liquid may be a solvent, such as, for example, a polar solvent, including water, or an aqueous liquid, for example, water or other aqueous solution comprising, for example, a detergent and/or active ingredient, such as, for example, acid, base, enzyme, to remove traces of test liquid.

Dispensing a volume V2 equal or smaller than V4 minus V1 of the test liquid into the wash liquid can mean dispensing part of the aspirated volume V4 into the wash liquid while the nozzle is dipped into the wash liquid. Also in this case, the volume V2 can be nominal, meaning that the pipetting unit can be operated such as to pump out, i.e. dispense, a volume V2. However, the effectively dispensed volume may comprise air and therefore may be smaller than the nominal volume V2. In any case, by this step, a plug of test liquid having a volume equal or greater than V1 can be brought to the extremity of the nozzle and traces of test liquid on the outside of the nozzle can be washed away.

The method can further comprise dipping the nozzle into a reaction liquid and dispensing the volume V1 of test liquid required for the test. This can mean moving the nozzle towards and into the reaction liquid so that the nozzle can be positioned at a depth below the surface, which can be sufficient for dispensing the desired volume directly into the reaction liquid. This depth can be typically in the order of a few millimeters, e.g. less than about 5 mm, in order to minimize contact of the outside of the nozzle with the reaction liquid. In this way, the risk of carryover and disruption of the volumetric ratio between test liquid and reaction liquid, due to external wetting of the nozzle, can be reduced. Dispensing the volume V1 can mean pumping out a volume, which can correspond to the volume of test liquid required for the test directly into the reaction liquid.

In order to make sure that an effective volume of test liquid, which can correspond to V1, can be dispensed, V4 may be large enough so that the total aspirated volume V4 of test liquid can be the sum of three test liquid volumes V1, V2, and V3 wherein V3 can be an excess of test liquid remaining in the pipetting unit after dispensing V1 in the reaction liquid. Having an excess of test liquid V3 may be useful also to minimize possible dilution effects due to possible contact between the test liquid and a system liquid if present. This can means that the volume of test liquid V1 dispensed into the reaction liquid can be less likely to contain system liquid if an excess of test liquid V3 can be present between V1 and the test liquid. The risk can be further reduced if a plug of gas such as air is present between V3 and the system liquid.

According to one embodiment, V1, V2 and V3 can be each in the range of about 1 to about 100 microliters. According to one embodiment, V1 can be in the range of about 2 to about 50 microliters and V2 and V3 can be each in the range of about 1 to about 20 microliters. In particular, according to one embodiment, V1 may be different for different in vitro diagnostic tests requiring different volumes of test liquid for the test, while the volumes V2 and/or V3 can be constant. Thus the method may comprise aspirating different test liquid volumes V4 for different tests, which can require different volumes of test liquids V1, while keeping the volumes V2 and/or V3 constant.

According to one embodiment, wherein an excess of test liquid V3 can be left in the pipetting unit after dispensing V1, the method can further comprise dipping the nozzle into the wash liquid and dispensing the volume V3 in the wash liquid. This step can be analogous to the washing/dispensing step, wherein V2 can be dispensed into the wash liquid. This can mean moving the nozzle towards and into the wash liquid so that the nozzle can be positioned at a depth below the surface, which can be sufficient for washing that part of the outside of the nozzle contacted by the reaction liquid. The wash liquid and/or the wash chamber or vessel may be, for convenience, the same as used in the previous washing step or may be more suitably for this washing step. The effect of this step can be to wash the outside of the nozzle contacted by the reaction liquid and to avoid that the test liquid present in the nozzle contaminates the outside of the nozzle when dispensed. The pipetting unit may be thereby cleaned from the outside before the method is repeated with a new test liquid.

According to one embodiment, the method can comprise at least partially filling a fluidic system of the pipetting unit with a system liquid prior to aspirating the test liquid. A "system liquid" can herein be used to indicate a liquid associated with the pipetting operation of the pipetting unit and having the function to minimize dead volumes in the pipetting unit. This can mean minimizing the amount of compressible medium such as air in the fluidic system and thereby increasing the stiffness of the fluidic system and the precision of pipetting. The system liquid may be an aqueous liquid, for example, water or other aqueous solution. Alternatively, the system liquid may be a liquid immiscible with the test liquid. According to one embodiment, the system liquid can be the same as the wash liquid. According to one embodiment, the system liquid can be water and the wash liquid can be water.

According to one embodiment, the method can further comprise introducing a plug of gas in the pipetting unit prior to aspirating the test liquid so that the plug can be located between the system liquid and the test liquid after aspirating the test liquid. This plug can help to avoid or to minimize mixing between test liquid and system liquid, for example, by diffusion, which may result for example in dilution of the test liquid.

According to one embodiment, the method further can comprise dipping the nozzle into the wash liquid to wash at least part of the outside of the pipetting unit and dispensing a volume V5 of system liquid into the wash liquid for washing the inside of the pipetting unit. This step may be carried out together with the above step of dispensing the excess of volume V3 left in the pipetting unit after dispensing V1. This can mean that a volume of system liquid sufficient to wash the inside of the pipetting unit contacted by the test liquid can be pumped out of the nozzle in the same dispensing step, in which any excess volume V3 of test liquid can be dispensed into the wash liquid. Thus, in the same step, the system liquid, which can follow the test liquid, can wash the inside of the nozzle while the wash liquid, in which the nozzle can be dipped can wash the outside of the nozzle.

According to one embodiment, the method can comprise aspirating and/or dispensing at higher speed when aspirating/dispensing larger volumes of test liquids V4 and aspirating and/or dispensing at lower speed when aspirating/dispensing smaller volumes of test liquids so that the total aspiration/dispensing time can remain substantially constant for different volumes V4. In this way, the cycle time for different tests can remain unaffected by the pipetting operation regardless of the volume test liquid required for a test.

The present disclosure can also refer to a pipetting unit for pipetting a volume V1 of test liquid for carrying out an in vitro diagnostic test. The pipetting unit can comprise a fluidic system comprising at least one aspiration/dispensing nozzle to move at least in the vertical direction and to aspirate/dispense a volume of test liquid. The nozzle may be a reusable washable needle, for example, a steel hollow needle, or as a pipette tip, for example, a disposable pipette tip, for example, to be regularly replaced, for example, before pipetting a different test liquid. The pipetting unit may be mounted to a transfer head that can be moved in one or two directions of travel in a plane, for example, with guiding rails, and a third direction of travel orthogonal to the plane, for example, with a spindle drive.

The nozzle may penetrate the cap of a test liquid container and aspirate a volume V4 of test liquid through the cap.

The pipetting unit may further comprise a source of system liquid. In particular, the fluidic system may comprise tubing for fluidically connecting the source of system liquid with the nozzle and a system pump for pumping the system liquid through the fluidic system.

The pipetting unit may further comprise a pipette pump coupled to the fluidic system for aspirating/dispensing a test liquid by pumping the system liquid in the fluidic system away from/towards the nozzle respectively. The pump may be for example the syringe type or any other type known in the art and to pump volumes of liquids in the range of V4.

The pipetting unit may further comprise a controller to control the movement of the nozzle and the pumping of system liquid such as to dip the nozzle into a test liquid and aspirate a volume V4 of the test liquid larger than the volume V1 required for carrying out the test, dip the nozzle into a wash liquid and dispense a volume V2 equal or smaller than V4 minus V1 of the test liquid into the wash liquid, dip the nozzle into a reaction liquid and dispense the volume V1 of test liquid required for the test, dip the nozzle into the wash liquid to wash at least partially the outside of the pipetting unit and dispensing a volume V5 of system liquid into the wash liquid for washing the inside of the nozzle.

The controller may be, for example, a programmable logic controller running a computer-readable program provided with instructions to perform operations in accordance with an operation plan associated at least with the pipetting of test liquids. In particular, the operation plan may comprise operations other than aspirating, dispensing and moving the pipetting unit. For example, the operation plan may comprise one or more of the following: moving of test liquid containers, opening and/or closing of test liquid containers, piercing caps of test liquid containers, moving of reaction vessels, loading and/or disposing of pipette tips, mixing of test liquids, for example, by sip and spitting. In particular, the controller may comprise a scheduler, for executing a sequence of steps within a predefined cycle time. The controller may further determine the order of in vitro diagnostic tests according to the assay type, urgency, and the like.

The pipetting unit may comprise a pressure sensor for measuring a pressure internal to a test liquid container closed by a cap when the nozzle penetrates the cap. The controller may then control the pipetting unit such as to aspirate the test liquid only if the measured pressure is within a predefined range. In particular, since the pressure inside the container can play an important role for the precision of pipetting and the pipetting unit may be operate within an optimal pressure range; measuring the pressure in advance may spare unnecessary process steps. Thus, if the measured pressure is out of the predefined range, the controller may terminate the pipetting operation associated with that sample and proceed to wash the nozzle without carrying out an in vitro diagnostic test on that test liquid. In alternative, the pipetting operation may be continued and the result of the in vitro diagnostic test may be flagged as potentially incorrect due to incorrect pressure range in the test liquid container. Pressure sensors coupled to pipetting units are known in the art and are not further elucidated here.

The pipetting unit may comprise a liquid level detector to detect the surface of the test liquid to be aspirated. In such a case, the controller may control the movement of the nozzle and the pumping of system liquid based on the information of the liquid level detector. The liquid level detector may be of any kind known in the art, such as, for example, based on conductance or capacitance measurement, based on optical detection, based on detection of pressure changes, and the like. Liquid level detectors coupled to pipetting units are known in the art and are not further elucidated here.

According to one embodiment, the controller can regulate the pumping speed of system liquid and thereby the aspiration and/or dispensing speed based on the volume V4 of test liquid to be aspirated/dispensed respectively so that the total aspiration/dispensing time can remain substantially constant for different volumes V4.

The pipetting unit may be integrated, i.e. built in a work-cell or be a module of a system connected to a work-cell. A "work cell" can be either a stand-alone apparatus or a module within a larger instrument assisting users with in vitro diagnostic tests, such as, for example with qualitative and/or quantitative evaluation of samples for diagnostic purpose, and/or sorting and/or preparation of samples before detection, or storing and/or disposal of samples after detection. In particular, a work cell may be related to analytical and/or to pre-analytical and/or to post-analytical sample processing steps. Work-cells may be connected to each other and can depend at least in part on each other, for example, each carrying out a dedicated task of a sample processing workflow, which may be a prerequisite before proceeding to another work-cell. Alternatively, work cells may work independently from each other, for example, each carrying out a separate task, for example, a different type of analysis on the same sample or different sample. In general, a work cell may comprise units for loading and/or unloading and/or transporting and/or storing sample tubes or racks comprising sample tubes or multi-well plates, units for loading and/or unloading and/or transporting and/or storing reagent containers or cassettes, units for loading and/or unloading and/or transporting and/or storing and/or washing reaction vessels, for example, cuvettes, units for loading and/or unloading and/or transporting and/or storing pipette tips or tip racks. It may comprise identification units comprising sensors, such as, for example, barcode or RFID readers. It may comprise wash stations for washing pipette tips or needles or reaction vessels, such as, for example, cuvettes, mixing paddles, and the like.

Aspirating an excess of test liquid can ensure that a sufficient volume required for the test can be aspirated. Dispensing a part of the aspirated test liquid into a wash liquid can ensure that errors due to the position of the aspirated test liquid in the pipetting unit in the following dispensing step can be minimized. Dipping the pipetting unit in the wash liquid before dispensing a part of the aspirated test liquid can ensure that errors due to the surface effects of the nozzle can be minimized when dispensing and that the outside of the nozzle can be washed before the next step. Also, dipping the nozzle in the wash liquid can ensure that the pipetting conditions can be the same every time, as any trace of test liquid at the tip and sides of the nozzle can be replaced by wash liquid, without influence on the test, thus increasing reproducibility. Dipping the pipetting unit into a reaction liquid before dispensing the volume of test liquid required for the test can help ensure that errors due to the surface effects of the nozzle can be minimized.

The disclosed method can be particularly suitable for tests where the precision of pipetting can be more important than the risk of carryover. This can be, for example, the case for coagulation tests.

Referring initially to FIG. 1, FIG. 1 shows schematically an example of pipetting unit 100 for pipetting a volume V1 of liquid sample 10 for carrying out an in vitro diagnostic test. The pipetting unit 100 can comprise a fluidic system 51 comprising an aspiration/dispensing nozzle 50 to move at least in the vertical direction and to aspirate/dispense a volume of liquid sample 10. In particular, the nozzle 50 can penetrate a cap 11 of a sample tube 12 and can aspirate a volume V4 of liquid sample 10 contained therein. The cap 11 can comprise an elastomeric material sealing the sample tube 12 and the sample tube 12 can have an inner space 13, which can be partially evacuated. The pressure internal to the sample tube 12 can be therefore below the atmospheric pressure. In particular, the nozzle 50 can be a reusable steel needle, which can comprise an aspiration/dispensing opening at one end. The pipetting unit 100 can comprise a source 60 of system liquid 61 and a system pump 71 to at least partially fill the fluidic system 51 with system liquid 61 and to wash the inside of the fluidic system 51 with the system liquid 61 by pumping system liquid out of the nozzle 50. The system liquid 61 can be water. The pipetting unit 100 can further comprise a pipette pump 70 coupled to the fluidic system 51 for aspirating/dispensing a liquid sample 10 by moving the system liquid 61 in the fluidic system 51 away/towards the opening of the nozzle 50 respectively. The pipette pump 70 can be the syringe type having a volume to pipette at least a volume V4 of liquid sample 10.

The pipetting unit 100 can further comprise a controller 80 to control the movement of the nozzle 50 and the operation of the pump 70 such as to aspirate a volume V4 of liquid sample 10 and dispense a volume V1 of liquid sample into a liquid reagent 30, with washing and dispensing steps in between and after.

The pipetting unit 100 can further comprise a liquid level detector 90 to detect the level of the surface of the liquid sample 10 in the sample tube 12. The controller 80 can receive surface level information from the liquid level detector 90 and can move the nozzle 50 such as the opening can be positioned at a desired depth below the surface. The controller 80 then can control the pump 70 so that the desired volume V4 of liquid sample 10 can be aspirated.

The controller 80 can be further configured to regulate the pumping speed Ps of system liquid 61 and thereby the aspiration and/or dispensing speed of the pipette pump 70 based on the volume V4 of liquid sample 10 to be pipetted so that the total aspiration/dispensing time can remain substantially constant for different volumes V4.

The pipetting unit 100 can further comprise a pressure sensor 91 for measuring the pressure internal to the sample tube 12 and the controller 80 can control the pipetting unit 100 such as to aspirate the sample 10 only if the measured pressure is within a predefined range.

FIG. 1 also illustrates schematically a method of pipetting a liquid sample 10 using the pipetting unit 100 for carrying out an in vitro coagulation test. Consecutive steps are indicated by arrows from left to right. Starting from the second step, only the nozzle 50 is shown as component of the pipetting unit 100 for clarity reasons.

The method can comprises introducing air in the nozzle 50 prior to aspirating the liquid sample so that a plug of air 62 can be located between the system liquid 61 and the liquid sample 10 after aspirating the liquid sample 10.

The method can comprise detecting by the liquid level detector 90 the level of a liquid sample 10 in the sample tube 12, moving the nozzle 50 through the cap 11 of the sample tube 12 towards the surface of the liquid sample 10, dipping the nozzle 50 into the liquid sample 10 until the opening can be positioned at a desired depth below the surface level and aspirating a volume V4 of the liquid sample 10 larger than the volume V1 required for carrying out the in vitro diagnostic test. In one embodiment, the liquid sample 10 can be blood plasma treated with citrate.

The method can further comprise withdrawing the nozzle 50 from the sample tube 12. During this operation, air may be introduced into the nozzle 50 due to the elasticity of the air already present in the fluidic system 51 and the pressure change between the inside and outside of the sample tube 12. The total aspirated volume V4 can be thus the sum of the aspirated liquid sample volume V4' and of the aspirated air volume V4".

The method can further comprise dipping the nozzle 50 into a wash liquid 20 comprised in a wash chamber 22 and dispensing a volume V2 smaller than V4 minus V1 of the liquid sample 10 into the wash liquid 20, thereby dispensing also the plug of air V4" at the extremity of the nozzle 50. The dispensed test liquid V2 can be thus prevented from adhering to the outside of the nozzle 50 by surface tension. At the same time, the outside of the nozzle 50 in contact with the wash liquid 20 can be washed from possible traces of liquid sample 10 that may have adhered during the aspiration step. A volume of liquid sample 10 can remain in the nozzle 50, which corresponds to V1 plus an excess V3 of liquid sample 10, V1 plus V3.

The method can further comprise dipping the nozzle 50 into a liquid reagent 30 comprised in a reaction vessel 32 and dispensing the volume V1 of liquid sample 10, which can be required for the test, while leaving the excess volume V3 of liquid sample 10 in the nozzle 50.

The method can further comprise dipping the nozzle 50 into the wash liquid 20 and dispensing the volume V3 in the wash liquid 20. The method can further comprise dispensing a volume V5 of system liquid 61 into the wash liquid 20 in the same dispensing step, and thereby also the plug of air 62. In this way, both the inside of the nozzle 50 and the outside part of the nozzle 50 dipped into the wash liquid 50 can be washed. The nozzle 50 may be dipped into the wash liquid 20 to a greater depth with respect to the previous washing step such as to wash part of the outside of the nozzle penetrated through the cap 11 of the sample tube 12.

Since the position of the aspirated volume V4' of liquid sample 10 in the nozzle 50 can be imprecisely defined due to the effects described, the volumes V2 and V3 of effectively dispensed liquid sample 10 can be also imprecisely defined. However, the volume V1 of effectively dispensed liquid sample 10, which can be required for the test, can be well defined as it can be between the two volumes V2 and V3 of liquid sample 10 and can be unaffected by the air plugs neighboring V2 and V3. In other words, depending on the actual position of V4 in the nozzle 50, the dispensed volumes V2 and V3 may comprise different amounts of liquid sample 10 while V1 can remain unchanged.

The method may then be repeated for another sample, wherein the volume V1 and therefore the volume V4 may be different depending on the particular test to be carried out with that sample.

In particular, the method can comprise aspirating different test liquid volumes V4 for different tests, which can require different volumes of test liquids V1, while maintaining V2 and V3 constant. According to one example, V1 may vary from about 2 to about 50 microliters depending on the test. According to one example, V2 is about 5 microliters and V3 is about 8 microliters but V2 and V3 may be adapted according e.g. to the characteristics of the pipetting unit, such as size and internal volume of the nozzle 50. For example, in order to determine the activated partial thromboplastin time (APTT) or the prothrombin time (PT) of a sample 10, a total volume V4 of about 63 microliters of sample 10 can be aspirated, wherein the volume V1 of sample 10, which can be required and dispensed for the test, can be about 50 microliters. According to another example, in order to carry out an antithrombin (AT III) test, a total volume V4 of about 15 microliters of sample 10 can be aspirated, wherein the volume V1 of sample 10, which can be required and dispensed for the test, can be about 2 microliters.

The method can further comprise aspirating at a higher speed when aspirating larger volumes of test liquids V4 and aspirating at a lower speed when aspirating smaller volumes of test liquids V4, so that the total aspiration time can remain substantially constant for different volumes V4. The method can further comprise dispensing at a higher speed when dispensing larger volumes of test liquids V1 and dispensing at a lower speed when dispensing smaller volumes of test liquids V1 so that the total dispensing time can remain substantially constant for different volumes V4.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A pipetting unit for pipetting a volume (V1) of test liquid for carrying out an in vitro diagnostic test, the pipetting unit comprising:
   a fluidic system comprising an aspiration/dispensing nozzle to move at least in the vertical direction and to aspirate/dispense a volume of test liquid;
   a source of system liquid and a system pump coupled to the source and to at least partially fill the fluidic system with system liquid in order to minimize dead volumes in the pipetting unit;
   a pipette pump coupled to the fluidic system for aspirating/dispensing a test liquid by pumping the system liquid in the fluidic system away/towards an opening of the aspiration/dispensing nozzle respectively; and
   a controller programmed to control the movement of the aspiration/dispensing nozzle and the pumping of system liquid in order to dip the aspiration/dispensing nozzle into a test liquid and aspirate a volume (V4) of the test liquid larger than the volume (V1) required for carrying out the test, dip the aspiration/dispensing nozzle into a wash liquid and dispense a volume (V2) equal or smaller than (V4) minus (V1) of the test liquid into the wash liquid while the aspiration/dispensing nozzle remains immersed in the wash liquid, remove the aspiration/dispensing nozzle from the wash liquid and dip the aspiration/dispensing nozzle into a reaction liquid and dispense the volume (V1) of test liquid required for the test after dispensing the volume (V2) of the test liquid into the wash liquid, dip the aspiration/dispensing nozzle into the wash liquid to wash at least partially the outside of the pipetting unit and dispensing a volume (V5) of system liquid into the wash liquid for washing the inside of the nozzle.

2. The pipetting unit according to claim 1, wherein the aspiration/dispensing nozzle penetrates a cap of a test liquid container and aspirates a volume (V4) of test liquid through the cap.

3. The pipetting unit according to claim 2, further comprising,
   a pressure sensor for measuring a pressure internal to the test liquid container, wherein the controller controls the pipetting unit so that the pipetting unit aspirates the test liquid only if the measured pressure is within a predefined range.

4. The pipetting unit according to claim 1, further comprising,
   a liquid level detector to detect the surface of the test liquid to be aspirated, wherein the controller controls the movement of the aspiration/dispensing nozzle based on information of the liquid level detector.

5. The pipetting unit according to claim 1, wherein the controller regulates pumping speed (Ps) of system liquid and thereby aspiration and/or dispensing speed based on the volume (V4) of test liquid to be aspirated/dispensed respectively so that the total aspiration/dispensing time remains substantially constant for different volumes (V4).

* * * * *